United States Patent
Stanley et al.

(10) Patent No.: US 7,883,479 B1
(45) Date of Patent: Feb. 8, 2011

(54) STABILITY AUGMENTATION SYSTEM

(75) Inventors: Byron M. Stanley, Cambridge, MA (US); Thomas M. Stanley, Savannah, GA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 716 days.

(21) Appl. No.: 11/198,412

(22) Filed: Aug. 5, 2005

(51) Int. Cl.
*A61B 5/103* (2006.01)
*A61B 5/117* (2006.01)

(52) U.S. Cl. .................................................. 600/595

(58) Field of Classification Search ................ 600/595; 607/43, 115; 74/572.2; 73/379.01; 310/323.16, 310/358; 601/5
See application file for complete search history.

(56) References Cited

U.S. PATENT DOCUMENTS

| | | | | |
|---|---|---|---|---|
| 3,911,910 A | * | 10/1975 | Oesau | 602/2 |
| 4,912,351 A | * | 3/1990 | Takata et al. | 310/323.16 |
| 5,643,329 A | * | 7/1997 | Solomonow et al. | 607/43 |
| 6,234,045 B1 | * | 5/2001 | Kaiser | 74/572.2 |
| 6,458,089 B1 | * | 10/2002 | Ziv-Av | 600/595 |
| 6,487,906 B1 | * | 12/2002 | Hock | 73/379.01 |
| 6,695,794 B2 | * | 2/2004 | Kaiser et al. | 600/595 |
| 6,730,049 B2 | * | 5/2004 | Kalvert | 601/5 |

* cited by examiner

*Primary Examiner*—Max Hindenburg
*Assistant Examiner*—Adam J Eiseman
(74) *Attorney, Agent, or Firm*—AFMCLO/JAZ; William G. Auton; Thomas C. Stover

(57) ABSTRACT

A stability augmentation system for stabilizing human limbs from against limb tremors. The stability augmentation system includes: and arm brace; a plurality of piezoelectric sensors fixed on said arm brace for sensing angular motion about a first axis of a limb induced by alternating perturbations; and a plurality of piezoelectric actuators coupled to the limb and piezoelectric sensor, said piezoelectric actuator being responsive to the piezoelectric sensors for selectively applying a torque to the limb representative of the sensed angular motion such that the angular motion about the first axis induced by the perturbation is cancelled, said plurality of piezoelectric actuators concurrently applying a reactive torque, equal and opposite to the applied torque, to the limb.

7 Claims, 2 Drawing Sheets

STABILITY AUGMENTATION SYSTEM

STATEMENT OF GOVERNMENT INTEREST

The invention described herein may be manufactured and used by or for the Government for governmental purposes without the payment of any royalty thereon.

BACKGROUND OF THE INVENTION

The invention relates generally to electro mechanical and piezoelectric biomedical controllers, and more specifically, it relates to a stability augmentation system.

With old age, people tend to develop a jitter which is a direct result of degeneration of their nerves. Since both the nerves and the brain control area have degenerated to a point where there is a significant lag between knowledge of the position of the body part and commands from the brain that move the muscles and affect the position of the body part. Patented art of interest includes the following U.S. Patents, the disclosures of which are incorporated herein by reference:

U.S. Pat. No. 6,356,784, Mar. 12, 2002, Method of treating movement disorders by electrical stimulation and/or drug infusion of the pendunulopontine nucleus, Lozano, Andres M;

U.S. Pat. No. 6,695,794, Feb. 24, 2004, Active tremor control system, Kaiser, Kenneth W. et al;

U.S. Pat. No. 6,323,391, Nov. 27, 2001, Methods and transgenic mouse model for identifying and modulating factors leading to motor neuron degeneration, Schlaepfer, William W;

U.S. Pat. No. 5,643,329, Jul. 1, 1997, System for maintaining a desired spinal curvature of a user suffering from improper alignment of the vertebrae of the spine, Solomonow, Moshe;

U.S. Pat. No. 5,551,445, Sep. 3, 1996, Apparatus and method for movement coordination analysis, Nashner, Lewis M.;

U.S. Pat. No. 4,712,558, Dec. 15, 1987, Electrical stimulation of muscle, Kidd, Geoffrey;

U.S. Pat. No. 6,234,045, entitled Active Tremor Control issued to Ken Kaiser;

U.S. Pat. No. 6,839,594, entitled Actuation and Control of Limbs Through Motor Nerve Stimulation issued to Cohen et al.

The Lozano patent describes techniques for treating movement disorders by electrical stimulation and/or drug infusion. It utilizes an implantable signal generator and an electrode and/or an implantable pump and catheter. High electrical stimulation pulses and/or drug therapy is provided to the Pedunculopontine Nucleus (PPN). A sensor is also used to detect various symptoms of the movement disorders with a microprocessor algorithm to analyze the output from a sensor to regulate the stimulation and/or drug therapy delivered to the PPN.

The Schlaepfer patent describes methods of identifying factors involved in motor neuron degeneration by identifying factors affected by alterations in a C-binding complex of a ribonucleotide protein complex isolating and purifying the factors or nucleic acid sequences encoding the factors in a transgenic mouse.

The Solomonow patent describes a system for maintaining a desired spinal curvature of a user suffering from improper alignment of the vertebrae of the spine. In its broad aspects, it comprises a sensor feedback system and electrodes. The sensor feedback systems measures spinal curvature, determines whether selected conditions have been met warranting the application of electrical stimulation and provides information regarding the determination of an electronic stimulator. The electrodes are space ably mounted on selected portions of the user's back. They are in electrical communication with the electronic stimulator for casing contraction of the back muscles at selected levels, thus providing alignment of the spinal vertebrae. The sensor feedback system includes a sensor assembly which comprises an upper elongated rigid segment, a lower elongated rigid segment and a sensor.

U.S. Pat. No. 5,551,445 describes methods and devices are provided for evaluating among the limbs of a subject the distribution of impairments of the subject's ability to coordinate the muscular contractions to execute effective postural movements. The subject may be placed on two independently movable support surfaces, either of which may be fixed or sway-referenced. The subject's ability to maintain his or her equilibrium position is then monitored.

The Kidd patent describes a method and apparatus are disclosed for the electrotrophic stimulation of muscle, that is, stimulation using pulses trains onto which information which will cause long-term functional and/or structural changes in the muscle tissue. This information is coded into the interval between successive pulses of the series. Also disclosed is a method and apparatus for acquiring trophic data from motor until action potential series.

Patients with neurodegenerative diseases or trauma like cerebral infarct or spinal cord injury can have a variety of movement and muscle control problems, like resting, postural, intention or action tremor; dystonia (improper muscle tone); spasticity (undesirable movements, or muscle co-contraction); dyskinesia (poorly executed movements) or involuntary movements like ballismus, choreiform movements are torticollis (inappropriate movements or limbs control). Many of these problems can be called hyperkinesias. Although they can be chronic, or worse, progressive, they also may have times of relative remission. Such problems are found, at certain stages, for patients with Parkinson's disease, multiple sclerosis, cerebral palsey, secondary to deafferentation pain, post stroke, pose apoplexy or anoxia, post head or spinal trauma, post poisoning, cerebella disease etc. Dyskinesia also may result from long term usage of levodopa or other especially for Parkinson's patients.

A number of techniques are used for treating these and other movement disorders. Electrical stimulation and drug infusion techniques have become increasingly popular. In the case of electrical stimulation, an electrical lead having one or more electrodes is typically implanted near a specific site in the brain or spinal cord or a patient. The lead is coupled to a signal generator which delivers electrical energy through the electrodes to nearby neurons and neural tissue. The electrical energy delivered through the electrodes creates an electrical field causing excitation or inhibition of the nearby neurons. For example stimulation of the vagus nerve as described in U.S. Pat. Nos. 4,702,254; 4,867,164; and 5,025,807 has been used to reduce the likelihood that a person with epilepsy will experience a seizure. For example, U.S. Pat. No. 5,716,377 entitled "Method of Treating Movement Disorders by Brain Stimulation" discloses techniques for stimulation of various portions of the brain.

The systems cited above can be improved since the response delay can be directly modeled as a time lag in a control system. The system itself could theoretically be modeled, as least on first pass, as a linear second order system with a certain crossover and phase margin. The muscles provide a force and yield an acceleration. The eyes and other feedback mechanisms yield position (as well as velocity). As the response time increases, the modeled time delay increases. At a lower phase margin, the control system becomes oscillatory and marginally stable. There are higher orders damping terms that help keep the system stable where it would be modeled as unstable. The introduction of damping or additional feedback loops into this system could potentially stabilize or reduce jitter in the system. The likely result is a reduced bandwidth system that has a higher phase margin and lower crossover frequency.

SUMMARY OF THE INVENTION

The reader's attention is now directed towards FIG. 2. The present invention is a stability augmentation system for stabilization human limbs from against limb tremors. In one embodiment the stability augmentation system includes: an arm brace; a plurality of piezoelectric sensors fixed on said arm brace for sensing angular motion about a first axis of a limb induced by alternating perturbations; and a plurality of piezoelectric actuators coupled to the limb and piezoelectric sensor, and piezoelectric actuator being responsive to the piezoelectric sensors for selectively applying a torque to the limb representative of the sensed angular motion such that the angular motion about the first axis induced by the perturbation is cancelled, said plurality of piezoelectric actuators concurrently applying a reactive torque, equal and opposite to the applied torque, to the limb.

The stability augmentation system includes a feedback control system for measuring the angular rotation about said limb and the arm brace is a Velcro arm strap which holds and aligns the plurality of piezoelectric actuators along a path of an expected tremor.

The plurality of piezoelectric actuators includes a series of horizontal stacks each separated by a brace element such that the piezoelectric actuators have the dual ability to apply force based on electrical stimulation and to create a differential based on mechanical displacement.

DETAILED DESCRIPTION OF THE PREFERRED EMBODIMENT

The present invention includes a stability augmentation system similar to the above-cited Kaiser patent. In the present invention, the addition of another control loop to compensate for the jitter is proposed. The proposed solution can be implemented in a number of manners and fashions, including but not limited to, stimulating muscles with low voltage/current pulses, using piezoelectric actuators to apply pressure of force to the appropriate locations; sensing the motion of the muscles and firing of the nerves using electrodes or similar devices, as well as using pies-electric devices to both sense and gain energy from the movement of the body part. In additional the controller could be tuned to remove only certain frequencies of motion, in such as way as to only hinder the vibration and not the normal motion, in such as way as to only hinder the system might be less responsive at certain frequencies, but this might be an acceptable loss at times, such as when holding a knife or fork while eating.

Electrical methods would likely not be the way to go unless they could be implemented in such a way that they were not felt or were minimally bothersome. The key to the successful implementation will be in a simple, easy to use implementation—likely a fairly cheap medical device or aid—the equivalent of a knee brace or arm brace. In addition, finding the parts to push/pull/torque will be important in implementing the design. Muscle fibers or other electrically actuated devices could be used.

This could be used to build or exercise muscles, monitor patients movements or muscle strength over periods of time. Additions to the design could actually improve speed and motion. There is the potential to use this for military or hunting or any other case where stability of the arms is key.

As noted in prior art, human tremor is an involuntary trembling or shaking of the muscles of the body associated with physical weakness, emotional stress, or excitement. Tremor can detrimentally affect task performance for a number of different tasks including microsurgery, marksmanship, photography, videotaping and microcircuit assembly as well as the simple use of a pen by a person afflicted with mild Parkinson's disease.

Figure 1:
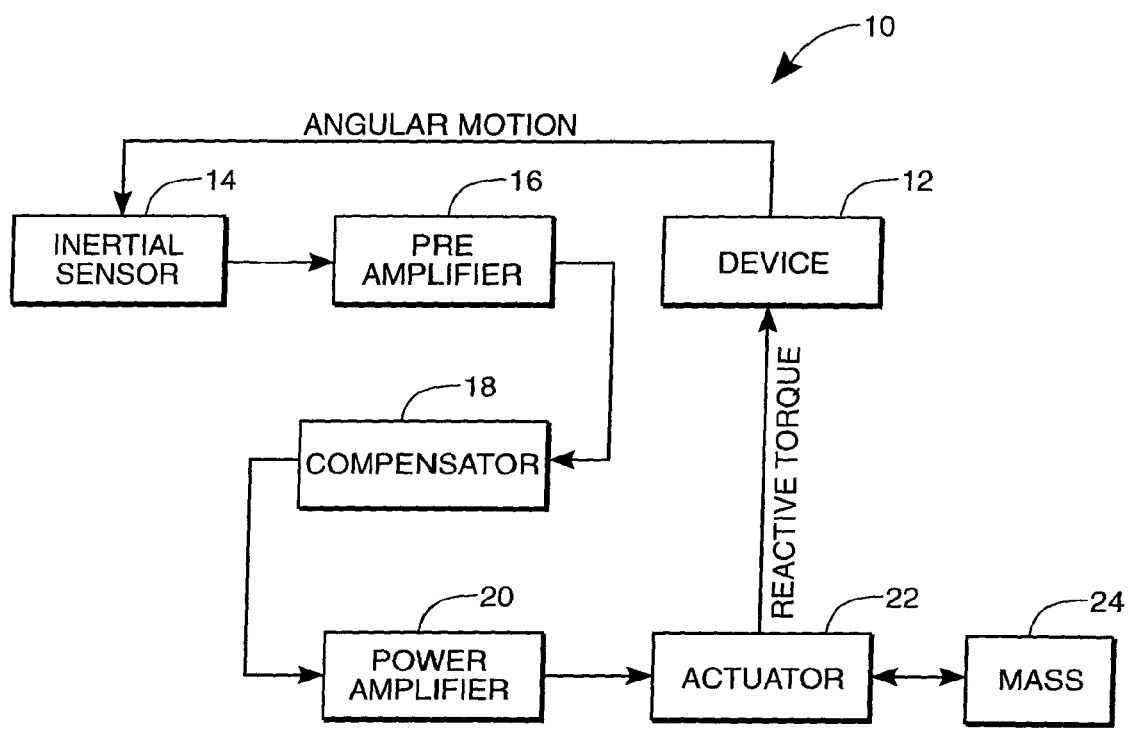
FIG. 1 is a prior art tremor control system useable by the present invention.

The reader's attention is directed towards FIG. 1, which is the prior act Active tremor control system 10, of the Kaiser patent, which provides stabilization of device subject to alternating perturbations, such as those experienced with human tremor. In Kaiser, Device 12 is any hand held device, for example a firearm, camera, scalpel, or writing implement. Device 12 is fitted with at least one inertial sensor 14 which senses motion about at least one control axis. This is not a necessary limitation of the invention, however, as additional sensors may be used depending on the number of degrees of movement to be monitored, e.g. pitch, yaw, or roll, or a single sensor may be used which senses motion about multiple axes.

Inertial sensor 14 detects angular motion about the control axis and sends a signal representative of the detected motion to preamplifier 16 which conditions and amplifies the signal. The conditioned signal is sent to compensator 18 which, in response, generates a reaction signal which is amplified by power amplifier 20 and then applied to actuator 22 coupled to device 12. Actuator 22, in response to the reaction signal generates a torque equal and opposite to the sensed angular motion and applies the torque to device 12. However, actuator 22 must simultaneously apply a reactive torque to independent mass 24, thereby allowing actuator 22 to "push" or mass 24 such that the angular motion about the control axis caused by the tremor is cancelled.

Thus, the closed loop system of the present invention satisfies Newton's third law of reaction force. The system quickly and effectively cancels the disturbance sensed by "pushing" on the mass, thereby allowing the torque applied to the device to cancel the alternating perturbations induced by tremor. This system, unlike the prior art, is a closed loop system which physically counteracts the disturbance rather than merely compensating for it.

Figure 2A:
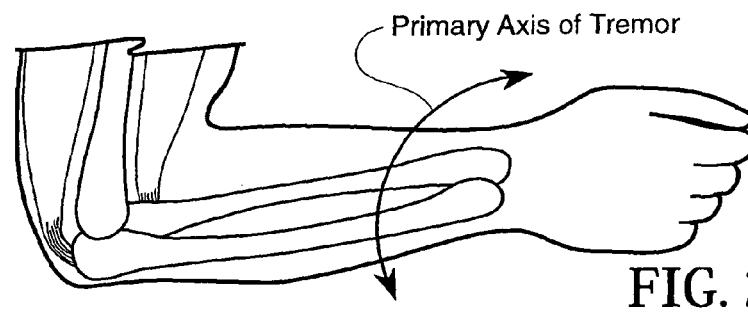
FIGS. 2a, 2b, and 2c illustrate the present inventions in use.
Figure 2B:
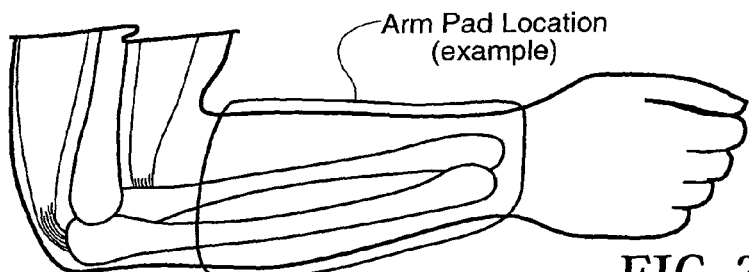
Figure 2C:
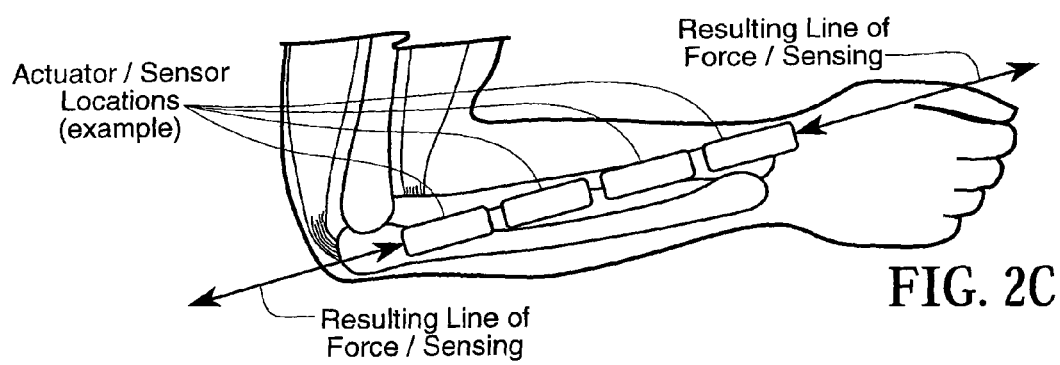

The reader's attention is now directed towards FIG. 2. The present invention is a stability augmentation system for stabilization human limbs from against limb tremors. In one embodiment the stability augmentation system includes: an arm brace; a plurality of piezoelectric sensors fixed on said arm brace for sensing angular motion about a first axis of a limb induced by alternating perturbations; and a plurality of piezoelectric actuators coupled to the limb and piezoelectric sensor, said piezoelectric actuator being responsive to the piezoelectric sensors for selectively applying a torque to the limb representative of the sensed angular motion such that the angular motion about the first axis induced by the perturbation is cancelled, said plurality of piezoelectric actuators concurrently applying a reactive torque, equal and opposite to the applied torque, to the limb.

The stability augmentation system includes a feedback control system for measuring the angular rotation about said limb and the arm brace is a Velcro arm strap which holds and aligns the plurality of piezoelectric actuators along a path of an expected tremor.

The plurality of piezoelectric actuators includes a series of horizontal stacks each separated by a brace element such that the piezoelectric actuators have the dual ability to apply force based on electrical stimulation and to create a differential based on mechanical displacement.

While the invention has been described in its presently preferred embodiment it is understood that the words which have been used are words of description rather than words of limitation and that changes within the purview of the appended claims may be made with departing from the scope and spirit of the invention in its broader aspects.

What is claimed is:

1. A stability augmentation system for stabilizing human limbs against limb tremors, comprising: a brace mountable to a limb;
a plurality of sensors mounted on said brace for sensing angular motion about a first axis of a limb, induced by alternating perturbations; a series of actuators coupled to said limb and one or more of said sensors, said actuators being responsive to said sensors for selectively applying a reactive torque to said limb, representative of the sensed angular motion such that the angular motion about said first axis, induced by the perturbation, is cancelled or dampened, said reactive torque being applied without pushing against an external mass member.

2. The stability augmentation system of claim 1 having an inertial sensor which includes a feedback control system for measuring the angular rotation about said limb.

3. The stability augmentation system of claim 2 in which said brace is a hook and loop strap which holds and aligns said actuators along the path of the expected tremor.

4. The stability augmentation system of claim 3 in which said actuators include a series of piezoelectric stacks as piezoelectric actuators, each separated by a brace element such that said piezoelectric actuators have the dual ability to apply expansion or contraction force based on electrical stimulation and to create a voltage differential based on mechanical displacement.

5. A stability augmentation system for stabilizing human limbs against limb tremors, comprising: a brace mountable to a limb;
a series of piezoelectric sensors/actuators mounted on said brace, producing sensor signals from sensing angular motion about a first axis of a limb, induced by alternating perturbations, said series of piezoelectric sensors/actuators coupled to said brace and said limb, said piezoelectric sensors/actuators being responsive to said sensor signals for selectively applying a reactive torque to said limb, representative of the sensed angular motion, such that the angular motion about the first axis, induced by the perturbation is cancelled or dampened, said reactive torque being applied without pushing against an external mass member.

6. The stability augmentation system of claim 5 in which the sensors/actuators include a feedback control system for measuring the angular rotation about said limb.

7. The system of claim 1 wherein said brace is a resilient pad which is adapted for snug fit to said limb, said actuators being rigidly connected to each other in series to cumulatively expand and contract, which series is mounted to said brace pad so that said actuators and pad can expand and contract on said limb to cancel or dampen tremors thereof.

* * * * *